United States Patent [19]

Ibrahim et al.

[11] Patent Number: 5,145,667

[45] Date of Patent: * Sep. 8, 1992

[54] COMPOSITIONS

[75] Inventors: Nader Ibrahim; Jeanette L. Sodano, both of Parsippany, N.J.

[73] Assignee: Beecham Inc., Philadelphia, Pa.

[*] Notice: The portion of the term of this patent subsequent to Jan. 15, 2008 has been disclaimed.

[21] Appl. No.: 520,793

[22] Filed: May 8, 1990

Related U.S. Application Data

[63] Continuation-in-part of Ser. No. 407,336, Sep. 14, 1989, Pat. No. 4,985,236, which is a continuation-in-part of Ser. No. 348,805, May 18, 1989, Pat. No. 4,923,684.

[30] Foreign Application Priority Data

Mar. 29, 1990 [GB] United Kingdom ............... 9007074

[51] Int. Cl.⁵ .......................... A61K 7/16; A61K 7/18
[52] U.S. Cl. .......................................... 424/52; 424/57
[58] Field of Search ....................................... 424/52, 57

[56] References Cited

U.S. PATENT DOCUMENTS

| | | | |
|---|---|---|---|
| 3,934,002 | 1/1976 | Haefele | 424/54 |
| 4,046,872 | 9/1977 | Mitchell et al. | 424/52 |
| 4,075,317 | 2/1978 | Mitchell et al. | 424/52 |
| 4,244,931 | 1/1981 | Jarvis et al. | 423/266 |
| 4,247,526 | 1/1981 | Jarvis et al. | 423/261 |
| 4,267,167 | 5/1981 | Weitzman et al. | 424/52 |
| 4,272,509 | 6/1981 | Wason | 424/49 |
| 4,340,583 | 7/1982 | Wason | 424/52 |
| 4,420,312 | 12/1983 | Wason | 51/308 |
| 4,421,527 | 12/1983 | Wason | 51/308 |
| 4,460,565 | 7/1984 | Weststrate et al. | 424/52 |
| 4,515,772 | 5/1985 | Parran, Jr. et al. | 424/57 |
| 4,627,977 | 12/1986 | Gaffar et al. | 424/52 |
| 4,806,342 | 2/1989 | Gaffar et al. | 424/52 |
| 4,808,400 | 2/1989 | Gaffar et al. | 424/52 |
| 4,808,401 | 2/1989 | Gaffar et al. | 424/52 |
| 4,842,847 | 6/1989 | Amjad | 424/52 |
| 4,889,713 | 12/1989 | Gaffar et al. | 424/52 |
| 4,894,220 | 1/1990 | Nabi et al. | 424/52 |
| 4,923,684 | 5/1990 | Ibrahim et al. | 424/52 |
| 4,927,625 | 5/1990 | Duckworth | 424/52 |
| 4,935,227 | 6/1990 | Duckworth | 424/52 |
| 4,937,066 | 6/1990 | Ulock | 424/52 |
| 4,980,153 | 12/1990 | Jackson et al. | 424/52 |
| 4,985,236 | 1/1990 | Ibrahim et al. | 424/52 |
| 4,988,499 | 1/1991 | Bristow et al. | 424/52 |
| 5,015,466 | 5/1991 | Parran et al. | 424/52 |
| 5,017,362 | 5/1991 | Gaffar et al. | 424/52 |
| 5,037,636 | 8/1991 | Chan | 424/52 |
| 5,037,637 | 8/1991 | Gaffar et al. | 424/52 |
| 5,043,154 | 8/1991 | Gaffar et al. | 424/52 |
| 5,094,843 | 3/1992 | Mazzanobile et al. | 424/52 |

FOREIGN PATENT DOCUMENTS

| | | |
|---|---|---|
| 236290 | 8/1987 | European Pat. Off. . |
| 254452 | 1/1988 | European Pat. Off. . |
| 295116 | 12/1988 | European Pat. Off. . |
| 61-36211 | 3/1986 | Japan . |
| 59-001409 | 6/1986 | Japan . |
| 63-005015 | 1/1988 | Japan . |
| 63-005016 | 2/1988 | Japan . |
| 63-141920 | 5/1988 | Japan . |
| 2188548 | 10/1987 | United Kingdom . |
| 2200551 | 8/1988 | United Kingdom . |

OTHER PUBLICATIONS

Briner et al Calc. Tiss. Res. 11 pp. 10–22 (1973).

*Primary Examiner*—Shep K. Rose
*Attorney, Agent, or Firm*—Rosenman & Colin

[57] ABSTRACT

The problem of providing a storage stable anti-calculus toothpaste comprising a tripolyphosphate salt is remedied by incorporating more than 4% of the salt and having the pH from about 8 to about 10. A tripolyphosphate salt may also be combined with a noncationic anti-bacterial agent such as triclosan to provide a composition having anti-calculus and anti-plaque activity.

15 Claims, No Drawings

COMPOSITIONS

This application is a continuation-in-part of our copending application Ser. No. 407,336, filed Sep. 14, 1989, now U.S. Pat. No. 4,985,236 which is a continuation-in-part of our co-pending application Ser. No. 348,805, filed May 8, 1989, now U.S. Pat. No. 4,923,684, issued May 8, 1990, both of which applications are incorporated herein by reference thereto.

The present invention relates to oral hygiene compositions, in particular compositions comprising a tripolyphosphate salt, which compositions are useful in the inhibition of dental calculus.

Several proposals for oral hygiene compositions comprising a tripolyphosphate salt as an anti-calculus agent have been made For instance, EP-A-0 236 290 (to Monsanto) discloses dentifrices comprising inter alia a tripolyphosphate salt in combination with an abrasive which is calcium pyrophosphate, the pH of which is preferably less than 8. EP-A-0 295 116 (to Unilever) discloses anti-calculus compositions comprising a combination of a tripolyphosphate salt and zinc citrate as the anti-calculus agent whilst EP-A-0 254 452 (to Lion Corporation) discloses anti-calculus compositions comprising a combination of a tripolyphosphate salt and anethol as the anti-calculus agent. Each of the two latter applications describes an example comprising a silica abrasive, with sodium tripolyphosphate included at 5% and 1.5% by weight of the composition, respectively. In neither case is any teaching provided with respect to the pH of the composition.

U.S. Pat. No. 4,627,977 (to Colgate-Palmolive) discloses anti-calculus compositions comprising a linear molecularly dehydrated polyphosphate salt such as a tripolyphosphate in which the otherwise observed enzymatic hydrolysis of the anti-calculus agent by phosphatase enzymes present in saliva is reduced by including a mixture of a source of fluoride ions and a synthetic anionic linear polymeric carboxylate. The preferred pH of such compositions is in the rante 5.5 to 8. The patent includes an example comprising sodium tripolyphosphate at 5% by weight of the composition.

In addition, GB-A-2 200 551 (to Colgate-Palmolive) discloses compositions having anti-calculus and anti-plaque activity, the former being provided by a linear molecularly dehydrated polyphosphate salt which is preferably a pyrophosphate salt, and the latter being provided by a non-cationic anti-bacterial agent such as a hydroxydiphenylether, and preferably triclosan. The preferred pH for such compositions is in the range 5.5 to 8. No examples comprising a tripolyphosphate are provided.

In spite of the various proposals referred to above, as far as we are aware, no anti-calculus dentifrice comprising a tripolyphosphate salt such as sodium tripolyphosphate has yet been marketed. One particular problem to be overcome in developing a commercially viable composition is that of the storage stability of the composition.

This problem is addressed in EP-A-0 236 290. This application provides storage stability data on two toothpastes comprising a calcium polyphosphate abrasive and sodium tripolyphosphate at 5% by weight of the composition, but which differ in having pHs of 8.5 and 7.1. Under accelerated aging conditions, both toothpastes suffer a similar loss of about one third in the amount of sodium tripolyphosphate present, suggesting that a higher pH per se is not a critical factor. This loss is considered to be unsatisfactory for a commercial product. JP-A-50161/88 (to Lion Corporation) suggests that storage stability may be improved by selecting as the abrasive certain silicas characterised by their surface area. There is however no discussion of the influence of pH or the amount of tripolyphosphate salt on storage stability. No storage stability data is provided in the other patent applications or patents referred to above.

It has now been found that the problem of storage stability may be remedied by providing a relatively large amount of the tripolyphosphate salt at a high pH, contrary to the teachings of the prior art.

Accordingly, in a first aspect, the present invention provides a toothpaste composition which comprises: an anti-calculus agent comprising at least about 4% by weight, based on the total weight of the toothpaste, of a water-soluble alkali metal tripolyphosphate salt; a dental abrasive other than calcium pyrophosphate; and an orally acceptable vehicle; the toothpaste having a pH of from about 8 to about 10.

Such a toothpaste is found to have sufficient storage stability for a commercially viable product.

It has been further found that an oral hygiene composition may be provided having, in addition to anti-calculus activity, anti-plaque activity by incorporating, in addition to a tripolyphosphate salt, an anti-bacterial compound.

Accordingly, in a second aspect of the invention, there is provided an oral hygiene composition which comprises: an anti-calculus agent comprising a water-soluble alkali metal tripolyphosphate salt; a substantially water insoluble noncationic anti-bacterial agent; and an orally acceptable vehicle.

Suitable noncationic anti-bacterial agents include for example diphenyl ethers of the formula (I):

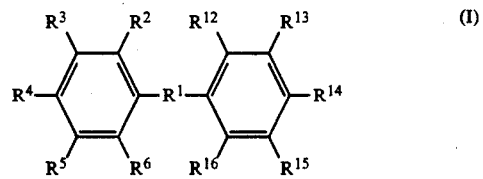

in which $R^1$ is oxygen, sulphur, or an alkylene group of from one to six carbon atoms and each of $R^2$ to $R^6$ and $R^{12}$ to $R^{16}$ is hydrogen, hydroxyl or a halogen; phenolic and bisphenolic compounds; benzoate esters and halogenated carbanilides.

Examples of compounds of formula (I) include, for example, 5,5'-dichloro-2,2'-dihydroxydiphenylmethane; 2,2'-dihydroxy-3,5,6,3',5', 6'-hexachlorodiphenyl; methane; 3,3'-dibromo-5,5'-dichloro-2,2'-dihydroxydiphenylether and 2,4,4'-trichloro-2'-hydroxydiphenyl ether (triclosan); of which triclosan is particularly preferred.

Examples of phenolic compounds, which include the halogenated salicylanilides, include, for example,
2-phenylphenol,
4-chlorophenol,
4-chloro-3-methylphenol,
4-chloro-3-methylphenol,
4-chloro-3,5-dimethylphenol,
2,4-dichloro-3,5-dimethylphenol,
5-methyl-2-pentylphenol,
4-isopropyl-3-methylphenol,
5-chloro-2-hydroxydiphenylmethane,
4',5-dibromosalicylanilide, 3,4',5-tribromosalicylanilide,
2,3,3',5-tetrachlorosalicylanilide,
3,3',4,5'-tetrachlorosalicylanilide,
3,5-dibromo-3'-trifluoromethylsalicylanilide, and
5-n-octanoyl-3'-trifluoromethylsalicylanilide Examples of bisphenolic compounds include, for example,
2,2'-methylenebis(3,4,6-trichlorophenol),
2,2'-methylenebis(4-chlorophenol),
2,2'-methylenebis(4-chloro-6-bromophenol),
bis(2-hydroxy-3,5-dichlorophenyl)sulphide, and
bis(2-hydroxy-5-chlorophenyl)sulphide.

Examples of benzoate esters include, for example, esters of hydroxybenzoic acid, especially the methyl, ethyl, propyl, isopropyl, butyl, isobutyl, hexyl, heptyl and benzyl esters.

Examples of halogenated carbanilides include, for example,
3,4,4'-trichlorocarbanilide,
3-trifluoromethyl-4,4'-dichlorocarbanilide, and
3,3',4-trichlorocarbanilide.

The preferred noncationic anti-bacterial agents are compounds of formula (I), in particular the compound triclosan.

The noncationic anti-bacterial agent is preferably present in from 0.01 to 2.0%, more preferably 0.05 to 1.0% by weight of the composition.

The oral hygiene composition may be presented in any of the conventional formulations such as a dentifrice, including toothpaste, a mouthwash or a formulation that is chewed or sucked by the user such as a lozenge or a chewing gum. Suitably the oral hygiene composition is in the form of a toothpaste composition which comprises an abrasive.

It will be appreciated that the alkali metal tripolyphosphate salt is included in compositions of the invention as an anti-calculus agent. In some instances, the anti-calculus agent may consist essentially of the water-soluble alkali metal tripolyphosphate salt.

Suitable water-soluble alkali metal salts include sodium or potassium tripolyphosphate which may be used in the hydrated or unhydrated forms. Preferably the tripolyphosphate salt is present in at least 4%, more preferably from about 4 to about 6% by weight, based on the total weight of the composition.

Preferably the pH of the composition is from about 8 to 10, more preferably from about 8 to about 9. When the composition comprises a compound of formula (I), a pH of above 8 is found to enhance the availability of the compound of formula (I). All references to the pH of the composition herein are references to the pH of the composition measured without dilution of the composition.

Suitable abrasives for use in the present invention include silica, plastics particles, alumina, calcium carbonate, and zinc orthophosphate, and if a noncationic antibacterial agent as hereinbefore defined is present, calcium pyrophosphate. Silica is especially preferred.

Silica abrasives are well known and commercially available, generally having an average particle size ranging between about 0.1 to about 30 microns, such as from about 5 to about 15 microns. Silica dental abrasives useful in the present invention include those marketed by the J. M. Huber Corporation under the trade name 'Zeodent' and the silica zerogels marketed by the W. R. Grace and Company, Davison Chemical Division under the trade name 'Syloid' U.S. Pat. No. 3,358,230 and U.S. Pat. No. 3,862,307 describe silica dental abrasives that are useful in the toothpaste compositions according to the present invention. The silica abrasive may also be a naturally occurring amorphous silica such as diatomaceous earth. Suitable forms of diatomaceous earth are those marketed under the trade mark 'Celite' by Johns - Manville Products Corporation, for instance 'Celite Superfine Superfloss'.

Plastics dental abrasives are well known and are described in, for example, GB 939 230, GB 995 351 and GB 1 055 784, and U.S. Pat. No. 3,151,027.

Alumina abrasives are well known and commercially available. Preferably the alumina abrasive may be treated with a solution of a surface-treating agent which may be an alkali metal silicate, hydrogen peroxide, an acid or an organophosphorus compound, of which an alkali metal silicate is especially preferred, as described in U.S. Pat. No. 4,781,982 (to Aluminium Company of America).

A calcium carbonate abrasive is preferably used in conjunction with an ionic agent to suppress the formation of free calcium ions, such as an alkali metal carbonate or bicarbonate, or mixture thereof, as described in EP 0 092 929 (to Beecham Group p.l.c.).

Generally, an amount of the dental abrasive suitable for use in the toothpaste composition of the present invention will be empirically determined to provide an acceptable level of cleaning and polishing, in accordance with the techniques well known in the art. Suitably, the abrasive will be present in from about 5 to about 60%, preferably from about 5 to about 30%, by weight of the toothpaste.

Advantageously, compositions of the present invention may further comprise a phosphatase enzyme inhibitor comprising a fluoride ion source, to optimise the anti-calculus activity of the compositions by inhibiting the enzymatic hydrolysis of the tripolyphosphate salt by salivary phosphatase enzymes. The fluoride ion source may be provided by an alkali metal fluoride, preferably sodium fluoride, an alkali metal monofluorophosphate, stannous fluoride and the like. Preferably, however, the fluoride ion source is an alkali metal fluoride, most preferably sodium fluoride, since this appears to provide enhanced storage stability as compared to other fluoride ion sources. The fluoride ion source serves as a phosphatase enzyme inhibitor, and in addition, the fluoride ion source may also provide an anti-caries effect. Preferably, the fluoride ion source will be used in an amount to provide an anti-caries effective amount and a phosphatase enzyme inhibiting amount, such as an amount sufficient to provide from about 25 ppm to about 3500 ppm, preferably about 1100 ppm, fluoride. It will be appreciated that the fluoride ion source may be included in compositions of the invention to provide a phosphatase enzyme inhibitor. In some instances, the phosphatase enzyme inhibitor may consist essentially of a fluoride ion source.

Suitably, in compositions of the present invention, the orally acceptable vehicle may comprise a thickening agent, a binding agent and a humectant. Preferred thickening and binding agents include for example natural and synthetic gums such as xanthan gums, carageens, alginates, cellulose ethers and esters and silica. When the abrasive is silica, it is preferred to use a thickening silica as the thickening agent. Preferred humectants include glycerin, sorbitol, propylene glycol and polyethylene glycol. A preferred humectant system consists of glycerin, sorbitol and polyethylene glycol.

In addition, the orally acceptable vehicle may optionally comprise surfactants, sweetening agents, flavouring agents, anticaries agents (in addition to the fluoride ion source provided as a phosphatase enzyme inhibitor), anti-plaque agents, anti-bacterial agents such as triclosan or cetyl pyridinium chloride, tooth desensitizing agents, colouring agents and pigments. Useful surfactants include the water-soluble salts of alkyl sulphates having from 10 to 18 carbon atoms in the alkyl moiety, such as sodium lauryl sulphate, but other anionic surfactants as well as non-ionic, zwitter-ionic, cationic and amphoteric surfactants may also be used.

When the preferred aqueous orally acceptable dental vehicle is employed, a toothpaste composition of the present invention suitably contains from about 10 to about 80% humectant, from about 0.25 to about 5% detergent, from 0 to about 2% sweeteners and flavouring agents together with water and an effective amount of binding and thickening agents, such as from about 0.1% to about 12%, to provide the toothpaste of the invention with the desired stability and flow characteristics.

Toothpaste compositions according to the present invention may be prepared by admixing according to conventional practice the tripolyphosphate salt, the dental abrasive and, if included, the fluoride ion source with the orally acceptable dental vehicle, which may be anhydrous but is preferably an aqueous orally acceptable dental vehicle, to form a storage stable semi-solid extrudable material useful as a toothpaste The pH thereof may be adjusted if necessary and desired, by the addition of, for instance sodium hydroxide. Preferably, the tripolyphosphate salt is in powder form when incorporated into the vehicle, as this tends to enhance the stability of the resulting toothpaste.

Toothpaste compositions of the present invention may also be prepared in the form of a paste of a uniform colour or in the form of a striped toothpaste. A suitable aparatus for filling toothpaste tubes with striped toothpaste is described in GB 962 757. In accordance with this patent, toothpastes of different colours are fed through separate tubes of a bundle of tubes that is inserted into a toothpaste container and gradually moved relative to the container as the container is filled.

In a third aspect, the present invention provides a method of inhibiting dental calculus which method comprises applying an anti-calculus effective amount of a composition as hereinbefore defined to the oral cavity; and optionally a method of also inhibiting dental plaque, when a compound of formula (I) is also present in the composition.

The invention will now be illustrated by the following examples:

EXAMPLE 1

A toothpaste was prepared from the following ingredients, sodium tripolyposphate being in powder form when combined with the other ingredients:

|  | % w/w |
|---|---|
| Polyethylene glycol (PEG-8) | 3.00 |
| Xanthan Gum | 0.70 |
| D + C Red No. 30 Lake | 0.02 |
| FD + C Blue No. 1 (0.2%) | 0.17 |
| D + C Yellow No. 10 (0.20%) | 0.24 |
| Sodium Fluoride | 0.24 |
| Sorbitol (70%) | 29.61 |
| Sodium Saccharin | 0.21 |
| Thickening Silica | 8.00 |
| Abrasive Silica | 14.00 |
| Titanium Dioxide | 0.96 |
| Glycerine 99% | 10.00 |
| Sodium Tripolyphosphate (Food Grade)* |  |
| Sodium Hydroxide (25%) | 1.80 |
| Flavour | 0.80 |
| Sodium Lauryl Sulphate | 1.15 |
| Deionized Water to | 100.00 |

*Food grade has a nominal purity of 92%.
Initial pH 8.4

EXAMPLES 2—5—STRIPED DENTIFRICES

The preparation of striped dentrifrices is well known in the art. U.S. Pat. Nos. 3,996,863, 3,980,767, 4,328,205 and 4,358,437 described toothpastes and methods for production thereof which may be utilised for the production of the dentifrices according to the present invention;

EXAMPLE 2

A striped dentifrice according to the present invention and comprising a central core with red stripes and aqua stripes was prepared by combining the ingredients set forth below according to known conventional techniques.

|  | % w/w | | |
|---|---|---|---|
|  | Core | Red | Aqua |
| PEG* 400 | 3.00 | 3.00 | 3.00 |
| Xanthan Gum | 0.70 | 0.70 | 0.70 |
| Sodium Fluoride | 0.24 | 0.24 | 0.24 |
| Sodium Saccharin | 0.21 | 0.21 | 0.21 |
| Triclosan | 0.20 | 0.20 | 0.20 |
| Sorbitol (70%) | 29.09 | 29.09 | 29.09 |
| FD + C Blue No. 1 dye | — | — | 0.0020 |
| D + C Yellow No. 10 dye | — | — | 0.0002 |
| Titanium Dioxide | 1.459 | — | — |
| Abrasive Silica | 14.00 | 14.00 | 14.00 |
| Thickening Silica | 8.00 | 8.00 | 8.00 |
| Sodium Tripolyphosphate | 5.00 | 5.00 | 5.00 |
| Glycerine | 10.00 | 10.00 | 10.00 |
| NaOH | 0.45 | 0.45 | 0.45 |
| Flavour | 0.80 | 0.80 | 0.80 |
| Sodium Lauryl Sulphate | 1.15 | 1.15 | 1.15 |
| Deionized Water to | 100.00 | 100.00 | 100.00 |

*PEG denotes polyethylene glycol.

EXAMPLE 3

As Example 2 but with trisclosan at 0.3%.

EXAMPLE 4

|  | % w/w | | |
|---|---|---|---|
|  | Core | Red | Aqua |
| PEG* 300 | 3.00 | 3.00 | 3.00 |
| Xanthan Gum | 0.60 | 0.60 | 0.60 |
| Sodium Fluoride | 0.22 | 0.22 | 0.22 |
| Sodium Saccharin | 0.20 | 0.20 | 0.20 |
| Triclosan | 0.20 | 0.20 | 0.20 |
| Sorbitol (70%) | 27.70 | 27.70 | 27.70 |
| FD + C Blue No. 1 dye | — | — | 0.002 |
| D + C Yellow No. 10 dye | — | — | 0.001 |
| D + C Yellow No. 3 dye | — | 0.10 | — |
| Titanium Dioxide | 1.45 | — | — |
| Abrasive Silica | 14.00 | 14.00 | 14.00 |
| Thickening Silica | 7.00 | 7.00 | 7.00 |
| Sodium Tripolyphosphate | 5.00 | 5.00 | 5.00 |

-continued

|  | % w/w | | |
| --- | --- | --- | --- |
|  | Core | Red | Aqua |
| Glycerine | 20.00 | 20.00 | 20.00 |
| Flavour | 0.80 | 0.80 | 0.80 |
| Sodium Lauryl Sulphate | 1.70 | 1.70 | 1.70 |
| Deionized Water to | 100.00 | 100.00 | 100.00 |

*PEG denotes polyethylene glycol.

EXAMPLE 5

As Example 4 but with triclosan at 0.3%.

EXAMPLE 6

Toothpastes A (as per Example 1), B, C, and D were prepared using a silica dental abrasive, sodium tripolyphosphate (STP), and sodium fluoride in an amount to provide 1100 ppm fluoride, in an aqueous orally acceptable vehicle. The amounts of STP and the pH of the toothpastes were varied as shown in the Table below:

TABLE

| Tooth-paste | pH* | STP % | % STP As % Of Initial STP After | | | |
| --- | --- | --- | --- | --- | --- | --- |
|  |  |  | 1 year | 2 year | 3 year | 5 year |
| A | 9 | 4.3 | 98 | 96 | 94 | 91 |
| B | 7 | 4.3 | 96 | 93 | 89 | 85 |
| C | 9 | 3.0 | 90 | 80 | 69 | 59 |
| D | 7 | 2.8 | 85 | 70 | 55 | 39 |

*The pH's reported are nominal values.

The data presented in the Table were derived from storage stability tests on actual samples of the four toothpastes, with the storage stabilty data regressed to provide predicted stability over four years of storage at room temperature with a confidence level of 95%.

As can be seen from the table, toothpaste A which contains a large amount of STP and has a high pH is the most stable of the four toothpastes.

In comparison, either a large amount of STP (B) alone or a high pH (C) alone provides inferior storage stability.

Unexpectedly, the use of a large amount of STP and a high pH in combination with a silica dental abrasive and a fluoride ion source provides sufficient storage stability for a commercial toothpaste.

We claim:

1. A storage-stable toothpaste, which consists essentially of at least about 4% of a water soluble alkali metal tripolyphosphate salt, from 0.05 to 1.0% by weight of a substantially water insoluble non-cationic anti-bacterial agent, a phosphatase enzyme inhibitor consisting of a fluoride ion source in an amount sufficient to supply about 25 ppm to about 3500 ppm of fluoride, from about 5 to about 60% by weight of a dental abrasive, and an orally acceptable vehicle, the composition having a pH of from about 8 to about 10.

2. A toothpaste as claimed in claim 1 in which the noncationic anti-bacterial agent is present in from 0.01 to 2.0% by weight of the composition.

3. A toothpaste as claimed in claim 1 in which the noncationic anti-bacterial agent is selected from the group consisting of diphenyl ether of the formula (I):

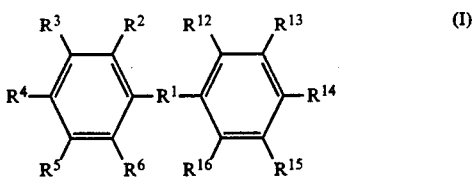

in which $R^1$ is oxygen, sulphur, or an alkylene group of from one to six carbon atoms and each of $R^2$ to $R^6$ and $R^{12}$ to $R^{16}$ is hydrogen, hydroxyl or a halogen; a phenolic or bisphenolic compound; a benzoate ester and a halogenated carbanilide.

4. A toothpaste as claimed in claim 3 in which the compound of formula (I) is selected from the group consisting of 5,5'-dichloro-2,2'-dihydroxydiphenylmethane; 2,2'-dihydroxy-3,5,6,3',5',6'-hexachloridiphenylmethane, 3,3'-dibromo-5,5'-dichloro-2,2'-dihydroxydiphenylether, and 2,4,4'-trichloro-2'-hydroxydiphenylether.

5. A toothpaste as claimed in claim 1 in which the abrasive is selected from silica, plastics particles, alumina, calcium carbonate, zinc orthophosphate or calciium pyrophosphate.

6. A toothpaste as claimed in claim 1 in which the abrasive is silica and the orally acceptable vehicle comprises a thickening silica.

7. A toothpaste as claimed in claim 1 in which the alkali metal tripolyphosphate salt is sodium or potassium tripolyphosphate.

8. A toothpaste as claimed in claim 1 in which the alkali metal tripolyphosphate salt is present in from about 4 to about 6% by weight of the composition.

9. A toothpaste as claimed in claim 1 in which the pH of the composition is from about 8 to about 9.

10. A toothpaste as claimed in claim 1 in which the the fluoride ion source is an alkali metal fluoride.

11. A toothpaste as claimed in claim 10 in which the alkali metal fluoride is sodium fluoride.

12. A toothpaste as claimed in claim 1 in which the orally acceptable vehicle comprises a humectant system which consists of glycerin, sorbitol and polyethylene glycol.

13. A toothpaste as claimed in claim 1 in the form of a striped toothpaste.

14. A method of inhibiting of dental calculus which method comprises applying an anti-calculus effective amount of a toothpaste as defined in claim 1 to the oral cavity.

15. A method of inhibiting dental calculus and dental plaque which method comprises applying an anti-calculus and anti-plaque effective amount of a toothpaste as defined in claim 1 to the oral cavity.

* * * * *